(12) United States Patent
Clement et al.

(10) Patent No.: US 9,387,185 B2
(45) Date of Patent: Jul. 12, 2016

(54) N$^{\omega}$-HYDROXY-L-ARGININE DERIVATIVES FOR THE TREATMENT OF DISEASES

(75) Inventors: Bernd Clement, Kiel (DE); Dennis Schade, Kiel (DE); Jürke Kotthaus, Kiel (DE)

(73) Assignee: Christian-Albrechts-Universität Zu Kiel, Kiel (DE)

( * ) Notice: Subject to any disclaimer, the term of this patent is extended or adjusted under 35 U.S.C. 154(b) by 427 days.

(21) Appl. No.: 13/143,156

(22) PCT Filed: Jan. 4, 2010

(86) PCT No.: PCT/DE2010/000001
§ 371 (c)(1),
(2), (4) Date: Sep. 23, 2011

(87) PCT Pub. No.: WO2010/078865
PCT Pub. Date: Jul. 15, 2010

(65) Prior Publication Data
US 2012/0123111 A1    May 17, 2012

(30) Foreign Application Priority Data
Jan. 9, 2009   (DE) .......................... 10 2009 004 203

(51) Int. Cl.
C07C 279/04    (2006.01)
C07H 15/04    (2006.01)
A61K 31/155    (2006.01)
A61K 31/7028    (2006.01)

(52) U.S. Cl.
CPC ........... *A61K 31/155* (2013.01); *A61K 31/7028* (2013.01); *C07C 279/04* (2013.01); *C07H 15/04* (2013.01)

(58) Field of Classification Search
CPC .............................. C07C 279/04; C07H 15/04
See application file for complete search history.

(56) References Cited

U.S. PATENT DOCUMENTS 6,277,884 B1     8/2001   De Tejada
2005/0158401 A1*  7/2005   Morris .......................... 424/682

FOREIGN PATENT DOCUMENTS

| WO | WO 01/32167 | 5/2001 |
| WO | WO 03/045369 | 6/2003 |
| WO | WO 2007005620 A2 * | 1/2007 |

OTHER PUBLICATIONS

Moali et al., "Óxidations of Nω-Hydroxyarginine Analogues and Various N-Hydroxyguanidines by NO Synthase II: Key Role of Tetrahydrobiopterin in the Reaction Mechanism and Substrate Selectivity", Chemical Research in Toxicology, vol. 14, pp. 202-210, 2001.
Labby et al., "Methylated Nω-Hydroxy-L-Arginine Analogous as Mechanistic Probes for the Second Step of the Nitric Oxide Synthase-Catalyzed Reaction", Biochemistry, 52, pp. 3062-3073, 2013.
Schade et al., "Efficient Synthesis of Optically Pure Nω-Alkylated L-Arginines", Synthesis, No. 15, pp. 2391-2397, 2008.
Schade et al., "Prodrug Design for the Potent Cardiovascular Agent -Hydroxy-L-Arginine (NOHA): Synthetic Approaches and Physicochemical Characterization", Organic Biomolecular Chemistry, 9, pp. 5249-5259, 2011.

* cited by examiner

*Primary Examiner* — Samira Jean-Louis
(74) *Attorney, Agent, or Firm* — Diederiks & Whitelaw, PLC

(57) ABSTRACT

The present invention relates to physically-chemically and pharmacokinetically enhanced N$^{\omega}$-hydroxy-L-arginine (NOHA) derivatives and a method for producing the NOHA derivatives having enhanced physical-chemical and pharmacokinetic properties according to the invention.

5 Claims, 1 Drawing Sheet

N$^\omega$-HYDROXY-L-ARGININE DERIVATIVES FOR THE TREATMENT OF DISEASES

CROSS-REFERENCE TO RELATED APPLICATIONS

This application represents a National Stage application of PCT/DE2010/000001 entitled "N$^\omega$-Hydroxy-L-Arginine Derivatives for the Treatment of Diseases" filed Jan. 4, 2010, pending.

BACKGROUND OF THE INVENTION

1. Field of the Invention

The present invention relates to physically-chemically and pharmacokinetically enhanced N$^\omega$-hydroxy-L-arginine (NOHA) derivatives and a method for producing the NOHA derivatives having enhanced physical-chemical and pharmacokinetic properties according to the invention.

2. Discussion of the Prior Art

N$^\omega$-hydroxy-L-arginine is the physiologically occurring intermediate of the NO synthase catalysed oxidation L-arginine. NOHA is oxidised in a further step of NO synthase, nitrogen monoxide being released and L-citrulline being formed.

Thus the semi-essential amino acid L-arginine is the natural source for the nitrogen monoxide (NO).

Nitrogen monoxide (NO) is of decisive importance among others for supplying the organs with blood. NO leads indirectly to an increase of the vessels. The extent of the vascular dilation then has different effects in the individual organs. In the heart there is for example an improved circulation. In addition to expanding the vessels, NO also has other properties:

- The relaxing effect concerns not only the musculature of the vessels but also that of the bronchial tree.
- NO that is given off by the endothelial cells into the vessel lumen can prevent the accumulation of blood platelets (=thrombus formation).
- In the nervous system, it is an important signalling substance (transmitter) that influences the brain and gastrointestinal functions. Thus nerve ends situated in the intestinal wall cause a relaxation of the ring muscle due to the release of NO.
- NO is formed in defence cells (macrophages) and is capable of destroying bacteria. Stimulated by bacterial components (e.g. lipopolysaccharides) macrophages produce NO in high concentrations so that vital enzymes, e.g. those containing iron, are blocked. The conservation of meat for example by salting is based precisely on this process.

A dysregulation or reduced NO availability is thus related to diverse cardiovascular diseases. A limited NO availability is therefore associated with the so-called endothelial dysfunction—a state of multifactorial genesis—that is associated with high blood pressure, atherosclerosis, arterial thrombosis, coronary heart disease, heart failure, heart attack, hypercholesterolaemia and diabetes.

Old, rigid, atherosclerotically changed vessels can be deformed again with NO. Blood circulation is thus improved and among others high blood pressure can be normalised. For children that are born with serious respiratory dysfunction, the inhalation of NO is even today in use successfully. NO promotes the erection of the penis which has led to the development of drugs against impotence (Viagra®).

Also for fighting tumors it is expected that new treatments can be pursued with NO since NO produced by white blood cells does not only destroy bacteria but also cells.

However, NO has quite a short life. Within a short period it reacts with oxygen molecules to form nitrite ($NO_2^-$) and nitrate ($NO_3^-$). The short life also explains why NO can only be formed directly at its target.

It is further known that NOHA is a potent inhibitor of arginase I with a $K_i$ value between 30-42 μM.

In smaller in-vivo studies with rats, desired effects for treating the erectile dysfunction, endothelial dysfunction and hypertension could already be demonstrated using an i.v.-NOHA therapy.

Treating diseases associated with endothelial dysfunction, using conventional NO donors has a few disadvantages. In the case of nitrates for example the short therapeutic half time, the low oral bioavailability, partly adverse haemodynamic effects and tolerance effects are to be mentioned in this context. Indeed, a proatherogene effect during long-term treatment using organic nitrates is being discussed recently.

So that a therapy of NO-deficient diseases is possible with few side effects, the physiological situation has to be imitated as best as possible, i.e. NO must only be released for a short time, in the right amounts and of the right location. All these prerequisites are met using NOHA as an NO-donor or, to take into consideration the time factor, with a retarding prodrug of NOHA. In addition to the fact that using this strategy, nitrogen monoxide is only released where it is needed and is formed to an extent that is too small, the fact can be exploited that NOHA presents one of the most potent arginase inhibitors. Specifically an increased arginase activity is discussed as a mechanism for reduced NO availability and thus as a contributing factor in the development of the endothelial dysfunction. Thus a dual mode of action is exploited when using NOHA.

The use of L-arginine and N$^\omega$-hydroxy-L-arginine and their simple carboxylic acid esters, and also analogue N-hydroxyguanidine for treating a multiplicity of diseases, have been described and patented (a selection: WO03045369, U.S. Pat. No. 6,277,884, WO0132167, CA02386938).

In practice, use of such compounds is limited by their bad pharmacokinetic profile. The insufficient drug qualities of this substance can be explained above all by the presence of an unsubstituted N-hydroxyguanidine function. In particular, the following effects can be observed for the physical-chemical instability of N-hydroxyguanidines:

N-hydroxyguanidines decompose at room temperature and should be stored at 4-8° C., better −20° C. They are most stable in the form of their salts of strong acids. The following decomposition processes are known:

(1) Hydrolysis sensitivity: In particular at higher pH (>pH 7) conversion takes place to cyanamides and hydrolysis to ureas, which is relevant when taking into account the physiological pH of 7.4 in vivo.

(2) Oxidation sensitivity: The susceptibility to oxidation is probably the biggest issue of this class of substances since using many and very different oxidation agents it could be shown that two- and three-electron oxidation is possible. Using singly substituted aliphatic and aromatic hydroxyguanidines, oxidation potentials of $E_{ox1}$=+0.51-0.62 V and $E_{ox2}$=+1.14-1.81 V could be determined. The decomposition products can differ as a function of the oxidation agent. Also metal cations as for example iron (II)(III) or copper(II) favour such processes or participate in them. These processes are physiologically relevant since it is known that oxidative processes dominate in vivo and quite a range of physiological substances (reactive oxygen species, metal cations) favour these oxidation processes.

Metabolic instability of N-hydroxyguanidines:

N-hydroxyguanidines are effectively reduced in the body in an enzymatic catalysed manner to form corresponding guanidines. The enzyme systems responsible for this have already been partly identified. Thus the mitochondrial N-reduction is dependent on cytochrome b5, cytochrome b5 reductase and a molybdenum cofactor-dependent enzyme (mARC). The microsomale N-reduction is catalysed by cytochrome b5, cytochrome b5-reductase and a third component unknown so far.

In addition it is known that hydroxyguanidines can be O-glucuronidised within the framework of a metabolic phase II biotransformation to be converted into a form that can be excreted more easily.

This leads to a strong limitation of the biological half time as a result of thermal, hydrolytic, oxidative and enzymatic processes. Also a high first-pass effect is to be expected, considering the metabolic instability that was mentioned.

SUMMARY OF THE INVENTION

It is therefore the object of the invention to improve the physical-chemical and metabolic stability and thus the pharmacokinetic properties of $N^{\omega}$-hydroxy-L-arginine and their simple carboxylic acid esters as well as analogue N-hydroxyguanidines.

It was surprisingly found that by substituting the hydroxyguanidine function according to the invention thermal and oxidation-stable derivatives of the NOHA were produced for the first time. FIG. 1 shows a schematic overview of the inventive substitution of the NOHA derivatives.

The chemical formula of the inventive derivatives is shown below.

The inventive substitutions are marked by X. Both a substitution at the oxygen of the hydroxylic groups $X_2$ leads to surprisingly stable derivatives, as also a substitution at the nitrogen $X_1$ and also a combination of the two inventive substitutions. In a usual way, the carboxylic acid function can be esterified in a conventional manner with an alkyl or aryl radical or be present as an acid ($R_1$). Y can correspond to hydrogen, alkoxycarbonyl or aryloxycarbonyl radical. n can be 2 or 3. The chirality centre m can be R or S configured.

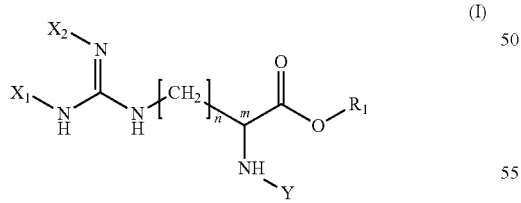

(I)

$X_{1,2}=$

(i)

(ii)

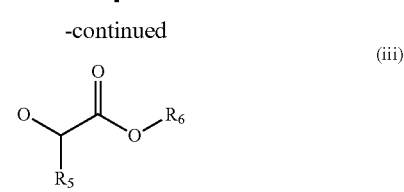

(iii)

(iv)

(v)

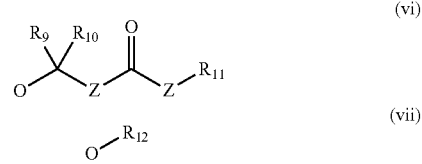

(vi)

(vii)

X=Teil eines Ringsystems=

(viii)

1,2,4-Oxadiazol-5-on

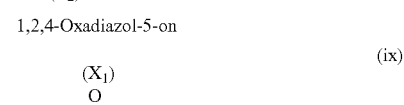

(ix)

1,5-Dioxa-2,4-diazinan

[X=part of ring system=]
where
$R_1$ can correspond to hydrogen, an alkyl or aryl radical; $X_1$ and $X_2$ can be identical or different and correspond to the structures (i-vii) (the exception is (i), where $X_1$ and $X_2$ have to be different; exempt is also $N^{\omega}$-hydroxy-L-arginine itself and its carboxylic acid esters), where $R_2$, $R_3$ and $R_4$ can correspond to hydrogen, alkyl or aryl radicals or can be shaped such that their structure corresponds to a monosaccharide(derivative) and $R_{5-12}$ can correspond to hydrogen, an alkyl or aryl radical; n corresponds to a number of methyl ($CH_2$) groups of 2-3; the chirality centre m can be R or S configured; Y can correspond to hydrogen, an alkoxycarbonyl or aryloxycarbonyl radical; Z can correspond to an oxygen or a nitrogen atom; $X_{1,2}$ are shaped such that they become part of ring systems having the structure (viii) or (ix), where $R_{13}$ and $R_{14}$ can correspond to hydrogen, alkyl or aryl radicals.

DETAILED DESCRIPTION OF THE INVENTION

Figure 1:
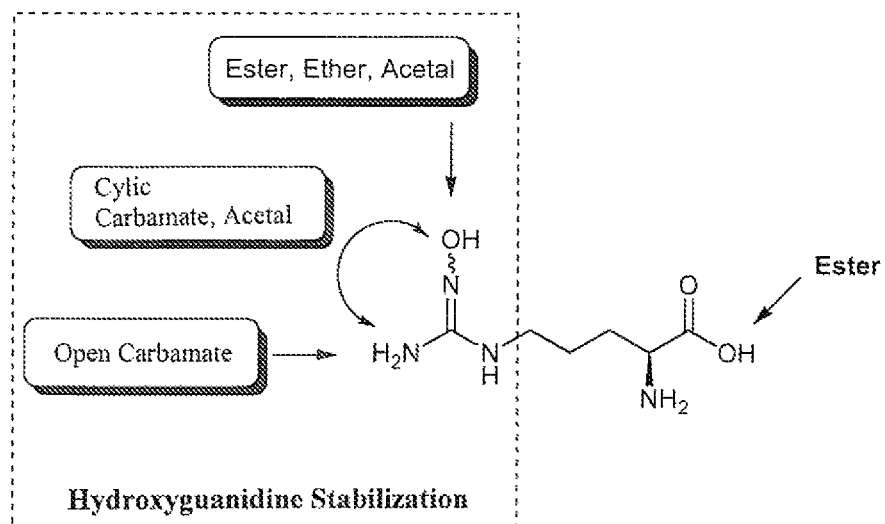
FIG. 1 shows a clear representation of the inventive optimisation of the drug properties of $N^{107}$-hydroxy-L-arginine (NOHA) as NO donor and arginase inhibitor for treating diseases.
Figure 2:
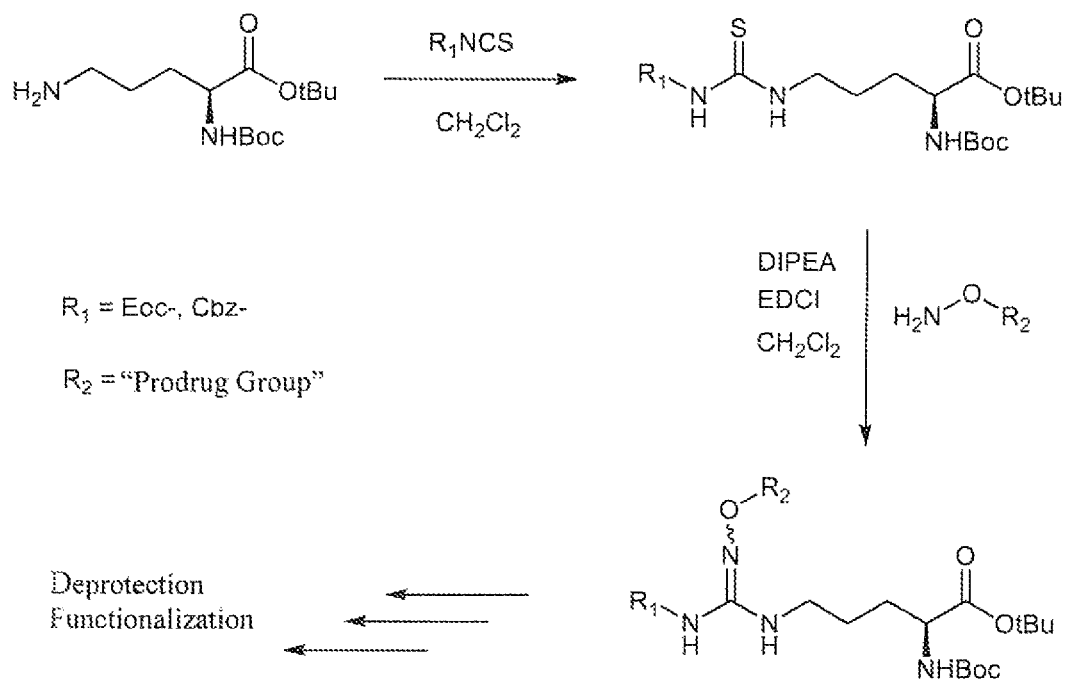
FIG. 2 For synthesising the inventive derivatives of the $N^{107}$-hydroxy-L-arginine a concept was developed that enables the illustration of very differently substituted compounds as represented by this figure. As an example, not limiting the generality of the teachings, the synthesis of NOHA derivatives of different types are described in the exemplary embodiments.

Material and Methods
Exemplary Embodiment 1: O-Alkylised NOHA Derivatives $N^\omega$-benzyloxycarbonyl-$N^\alpha$-(t-butyloxycarbonyl)-L-thiocitrulline-t-butylester (1)

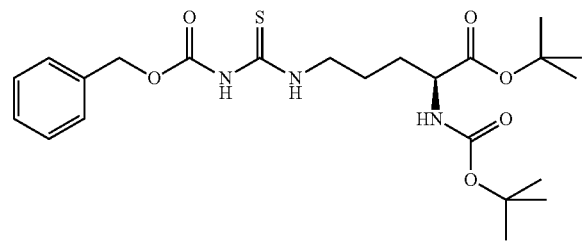 [SMILES: CC(C)(C)OC(=O)N[C@@H](CCCNC(=S)NC(=O)OCc1ccccc1)C(=O)OC(C)(C)C]

General regulation in the style of Linton et al. [J. Org. Chem. 2000, 65, 1566]:

7.0 mmol of $N^\alpha$-(t-butyloxycarbonyl)-L-ornithine-t-butylester are dissolved in 250 mL of dry dichloromethane. The solution is cooled to 0° C. and 14 mL of a 0.5 M solution (in dichloromethane) of benzyloxycarbonylisothiocyanate (7.0 mmol) are added in drops over 30 minutes. The reaction mixture is stirred for two hours, the solution being warmed to room temperature. Using a rotary evaporator, the mixture is concentrated to approximately one third of the original volume in vacuum and washed in each case with 25 mL of 1% HCl, water and saturated NaCl solution. The organic phase is dried over $Na_2SO_4$ and removed using the rotary evaporator. The thiourea 1 is mostly already >96% pure (DC) and is purified further using column chromatography.

After column chromatography over silica gel (cyclohexane/ethylacetate, 4:1), a light-yellow oil is obtained that becomes solid in the refrigerator.

Yield: 3.13 g (93%)
TLC: $R_f$=0.31 (cyclohexane/ethylacetate, 4:1; ninhydrine)
$^1$H-NMR (CDCl$_3$):
δ/ppm=1.44, 1.46 (s, 9H, 2×C(CH$_3$)$_3$), 1.64-1.75 (m, 4H, β,γ-CH$_2$) 3.66 (m, 2H, N—CH$_2$), 4.20 (m, 1H, α-CH), 5.08 (m, 1H, NH), 5.10 (s, 2H, CH$_2$-Cbz), 7.36 (m, 5H, ArH), 8.15 (br s, 1H, NH), 9.65 (br s, 1H, NH).
$^{13}$C-NMR (CDCl$_3$):
δ/ppm=24.8 (γ-CH$_2$), 28.7, 29.0 (2×C(CH$_3$)$_3$), 30.9 (β-CH$_2$), 45.8 (N—CH$_2$), 54.2 (α-CH), 68.8 (CH$_2$-Cbz), 80.4, 82.8 (2×C(CH$_3$)$_3$), 129.0, 129.4, 129.5 (ArCH), 135.2 (ArC), 153.2 (CO-Cbz), 156.0 (CO-Boc), 172.2 (COO$^t$Bu), 179.8 (C=S).
MS (ESI):
m/z=482 [M+H]$^+$, 426 [M–C$_4$H$_8$+H]$^+$, 370 [M–2×C$_4$H$_8$+H]$^+$, 326 [M–2×C$_4$H$_8$–CO$_2$+H]$^+$.
$C_{23}H_{35}N_3O_6S$ (481.61)

| Calculated | C | 57.36 | H | 7.33 | N | 8.73 |
| Found | C | 57.55 | H | 7.60 | N | 8.68 |

$N^\alpha$-(t-butyloxycarbonyl)-$N^\omega$-ethoxycarbonyl-L-thiocitrulline-t-butylester (2)

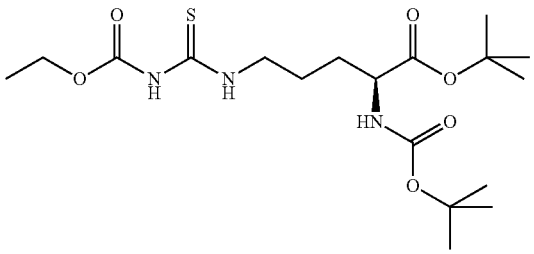 [SMILES: CCOC(=O)NC(=S)NCCC[C@H](NC(=O)OC(C)(C)C)C(=O)OC(C)(C)C]

8.0 mmol of $N^\alpha$-(t-butyloxycarbonyl)-L-ornithine-t-butylester are dissolved in 250 mL of dry dichloromethane. The solution is cooled to 0° C., and 927 mg ethoxycarbonylisothiocyanate (7.0 mmol), dissolved in 15 mL of dry dichloromethane, are added drop-wise over a period of 30 minutes. The reaction mixture is stirred at room temperature for two hours. The mixture is then concentrated using the rotary evaporator to approximately one third of the original volume and washed with in each case 25 mL of 1% HCl, water and saturated NaCl solution. The organic phase is dried over $Na_2SO_4$ and concentrated in vacuum. The thiourea 2 at this point is mostly already >than 96% pure (DC). The product is started to be dissolved in the solvent, activated carbon is added to it and it is cleaned by means of flash chromatography over a short silica gel column. A column with about 20 g of silica gel is used, and the eluent is cyclohexane/ethylacetate (4:1).

Yield: 2.76 g of a colourless oil (94%)
TLC: $R_f$=0.31 (cyclohexane/ethylacetate, 4:1; ninhydrine)
Melting point: 81° C.
$^1$H-NMR (CDCl$_3$):
δ/ppm=1.31 (t, 3H, $^3$J=7.1 Hz, CH$_2$—CH$_3$), 1.45, 1.47 (2×s, 9H, C(CH$_3$)$_3$, 1.61-1.90 (m, 4H, β,γ-CH$_2$), 3.66 (pseudo q, 2H, N—CH$_2$), 4.22 (q, 2H, $^3$J=7.1 Hz, CH$_2$—CH$_3$), 5.08 (m, 1H, α-CH), 8.06, 9.70 (2×br s, 1H, NH).
$^{13}$C-NMR (CDCl$_3$):
δ/ppm=14.9 (CH$_2$—CH$_3$), 24.9 (γ-CH$_2$), 28.7, 29.0 (2×C (CH$_3$)$_3$), 31.0 (β-CH$_2$), 45.8 (N—CH$_2$), 54.3 (α-CH), 63.4 (O—CH$_2$), 82.8 (C(CH$_3$)$_3$), 153.4 (CO-Boc), 156.2 (CO-Boc), 172.5 (COO$^t$/Bu), 180.1 (C=S).
MS (ESI):
m/z=442 [M+Na]$^+$, 420 [M+H]$^+$, 308 [M–2×C$_4$H$_8$+H]$^+$, 264 [M–2×C$_4$H$_8$—CO$_2$+H]$^+$.
$C_{18}H_{33}N_3O_6S$ (419.54)

| Calculated | C | 51.53 | H | 7.93 | N | 10.02 | S | 7.64 |
| Found | C | 51.68 | H | 7.97 | N | 10.06 | S | 7.62 |

N^ω-benzyloxycarbonyl-N^α-(t-butyloxycarbonyl)-N^ω-methoxy-L-arginine-t-butylester (3)

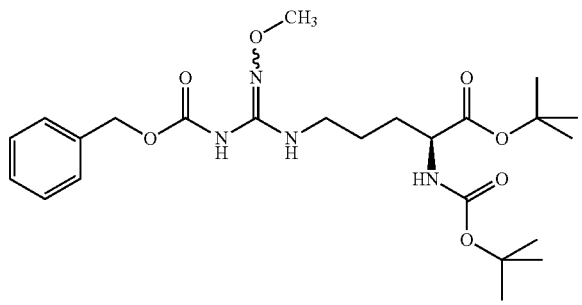 [SMILES: CON=C(NCCC[C@H](NC(=O)OC(C)(C)C)C(=O)OC(C)(C)C)NC(=O)OCc1ccccc1]

0.5 mmol of the thiourea 1 are dissolved in 5 mL of dry dichloromethane and 522 μL DIPEA (3 mmol) and 1.5 mmol of hydroxylammonia hydrochloride is added. The solution is brought to 0° C. for about 30 minutes and 287 mg N-ethyl-N'-(3-dimethylaminopropyl)carbodiimide hydrochloride (1.5 mmol) are added. Unless specified, the mixture is stirred over night at room temperature. The solution is diluted with approximately 10 mL of dichloromethane and washed in, each case with 5 mL of 1% HCl, water and saturated NaCl solution. The organic phase is dried over $Na_2SO_4$ and concentrated using the rotary evaporator. The result is mostly oils that are further purified using flash chromatography over, silica gel. The eluents used and the yields that were achieved are specified with the respective substances.

The eluent used is dichloromethane/methanol (99:1).
Yield: 235 mg of a colourless oil (95%)
TLC: $R_f$=0.30 (dichloromethane/methanol, 99:1; ninhydrine)

$^1$H-NMR (CDCl$_3$):
δ/ppm=1.44, 1.46 (2×s, 9H, C(CH$_3$)$_3$), 1.58-2.02 (m, 4H, β,γ-CH$_2$), 3.11 (m, 2H, N—CH$_2$), 3.66 (s, 3H, O—CH$_3$), 4.18 (m, 1H, α-CH), 5.11 (m, 1H, NH), 5.13 (s, 2H, CH$_2$-Cbz), 6.25 (m, 1H, NH), 7.36 (m, 5H, ArH), 7.91 (br s, 1H, NH).

$^{13}$C-NMR (CDCl$_3$):
δ/ppm=25.6 (γ-CH$_2$), 28.7, 29.0 (2×C(CH$_3$)$_3$), 30.9 (β-CH$_2$), 41.2 (N—CH$_2$), 54.5 (α-CH), 62.0 (O—CH$_3$), 68.3 (CH$_2$-Cbz), 80.3, 82.5 (2×C(CH$_3$)$_3$), 129.0, 129.3, 129.4 (ArCH), 135.8 (ArC), 148.8 (C=N), 153.6 (CO-Cbz), 156.0 (CO-Boc), 172.5 (COO$^t$Bu).

MS (ESI):
m/z=517 [M+Na]$^+$, 495 [M+H]$^+$, 439 [M–C$_4$H$_8$+H]$^+$.
C$_{24}$H$_{38}$N$_4$O$_7$ (494.58)

| Calculated | C | 58.28 | H | 7.74 | N | 11.33 |
| Found | C | 58.72 | H | 7.99 | N | 11.22 |

N^ω-methoxy-L-arginine Bis(trifluoracetate) (3)

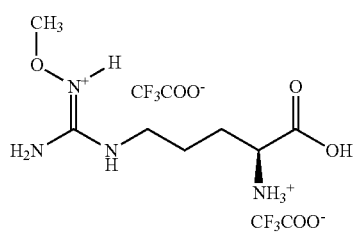

The protected L-arginine 3 (0.4 mmol) is stirred in 8 mL of TFA and 2.4 mL of thioanisol for 30 minutes at room temperature. Then the majority of TFA is distilled off in vacuum, and 5 mL of water and 15 mL of diethylether are added. The organic phase is also extracted twice using 5 mL of water, and the combined aqueous phases are finally washed with 5 mL of diethylether. The aqueous phase is concentrated using the rotary evaporator (at approximately 35° C.) and taken up with little 0.1% of TFA (in Aqua bidest.). Flash chromatography follows over an RP-18 column (eluent: 0.1% of TFA$_{(aq)}$), ninhydrine-positive fractions being combined. The combined fractions are concentrated to a volume of approximately 10 mL using the rotary evaporator and then lyophilised with freeze drying.

Yield: 171 mg of a colourless oil (99%), $R_f$=0.56 (i-propanol/water/acetic acid, 6:3:1; ninhydrine)

$^1$H-NMR (D$_2$O):
δ/ppm=1.78 (m, 2H, γ-CH$_2$), 1.99 (m, 2H, β-CH$_2$), 3.31 (t, 2H, $^3$J=6.8 Hz, N—CH$_2$), 3.75 (s, 3H, O—CH$_3$), 4.06 (t, $^3$J=6.2 Hz, 1H, α-CH).

$^{13}$C-NMR (D$_2$O, TPS):
δ/ppm=26.4 (γ-CH$_2$), 29.7 (β-CH$_2$), 43.0 (N—CH$_2$), 55.5 (α-CH), 67.3 (O—CH$_3$), 160.1 (C=N), 174.8 (CO).

HRMS (m/z):
calculated for C$_7$H$_{17}$N$_4$O$_3$ [M+H]$^+$=205.12952, found: 205.12951.

N^ω-methoxy-L-arginine-ethylester dihydrochloride (4)

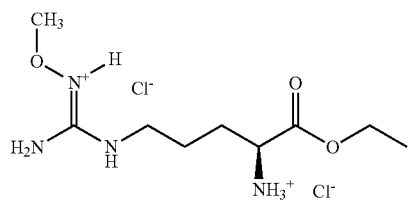 [SMILES: CCOC(=O)[C@@H]([NH3+])CCCN/C(N)=[NH+]/OC ; [Cl-] ; [Cl-]]

For the esterification, 238 mg of the free amino acid 3 (0.55 mmol) are dissolved in 5 mL of absolute ethanol in an argon atmosphere. The solution is stirred for 30 minutes at –10° C. before HCl gas is introduced into the solution for approximately 5-10 minutes. The batch is then stirred further for an hour at 0° C. and placed in the refrigerator for 36 hours. The solution is carefully concentrated at room temperature in vacuum and lyophilised. The product thus obtained is a very hygroscopic, amorph solid which liquefies on contact with air.

Yield: 168 mg of a clear oil (99%)
TLC: $R_f$=0.18 (i-propanol/water/acetic acid, 8:1:1; ninhydrine)

$^1$H-NMR (DMSO-d$_6$):
δ/ppm=1.24 (t, $^3$J=7.2 Hz, 3H, CH$_2$—CH), 1.47-1.90 (m, 4H, β,γ-CH$_2$), 3.22 (m, 2H, N—CH$_2$), 3.64 (s, 3H, O—CH$_3$), 3.99 (m, 1H, α-CH), 4.21 (q, $^3$J=7.2 Hz, 2H, CH$_2$—CH$_3$), 8.04 (br s, 2H, NH$_2$), 8.31 (br t, 1H, NH), 8.72 (br s, 3H, NH$_3^+$), 11.33 (br s, 1H, NH$^+$).

$^{13}$C-NMR (DMSO-d$_6$):
δ/ppm=13.9 (CH$_2$—CH$_3$), 24.0 (γ-CH$_2$), 27.0 (β-CH$_2$), 40.0 (N—CH$_2$), 51.4 (α-CH), 61.7 (CH$_2$—CH$_3$), 64.4 (O—CH$_3$), 157.2 (C=N), 169.2 (CO).

HRMS (m/z):
calculated for $C_9H_{21}N_4O_3$ [M+H]$^+$=233.16082, found: 233.16064.
$C_9H_{20}N_4O_3 \cdot 2.0HCl \cdot 0.7H_2O$ (317.82)

| | | | | | | |
|---|---|---|---|---|---|---|
| Calculated | C | 34.01 | H | 7.42 | N | 17.63 |
| Found | C | 33.65 | H | 7.66 | N | 18.20 |

$N^\alpha$-(t-butyloxycarbonyl)-$N^\omega$-ethoxycarbonyl-$N^{\omega'}$-methoxy-L-arginine-t-butylester (5)

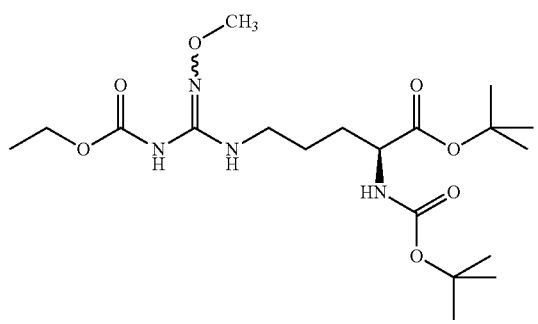 [SMILES: CCOC(=O)NC(=NOC)NCCC[C@H](NC(=O)OC(C)(C)C)C(=O)OC(C)(C)C]

210 mg of the thiourea 2 (0.5 mmol) are dissolved in 5 mL of dry dichloromethane and 261 μL of DIPEA (1.5 mmol) and 62.6 mg of methoxylamine hydrochloride (0.75 mmol) are added. The solution is brought to 0° C. for approximately 30 minutes and 143.5 mg of EDCl (0.75 mmol) are added. The mixture is stirred at room temperature over night. The solution is diluted with approximately 10 mL of dichloromethane and washed in each case with 5 mL of 1% HCl, water and saturated NaCl solution. The organic phase is dried over $Na_2SO_4$ and concentrated in vacuum. The raw product is further purified by means of column chromatography over silica gel (dichloromethane/methanol, 98:2).

Yield: 203 mg of a colourless oil (94%)

TLC: $R_f$=0.26 (dichloromethane/methanol, 98:2; ninhydrine)

$^1$H-NMR (CDCl$_3$):

δ/ppm=1.27 (t, $^3$J=7.1 Hz, 3H, CH$_2$—CH$_3$), 1.43, 1.45 (2×s, 9H, C(CH$_3$)$_3$), 1.56-1.89 (m, 4H, β,γ-CH$_2$), 3.09 (m, 2H, N—CH$_2$), 3.66 (s, 3H, O—CH$_3$), 4.16 (br q, $^3$J=7.1 Hz, 3H, CH$_2$—CH$_3$, α-CH), 5.10, 6.26 (2×br m, 1H, NH), 7.80 (br s, 1H, NH).

$^{13}$C-NMR (CDCl$_3$):

δ/ppm=14.9 (CH$_2$—CH$_3$), 25.6 (γ-CH$_2$), 29.7 (β-CH$_2$), 29.0, 30.9 (2×C(CH$_3$)$_3$), 41.2 (N—CH$_2$), 54.5 (α-CH), 62.0 (CH$_2$—CH$_3$), 62.6 (O—CH$_3$), 80.2, 82.5, (2×C(CH$_3$)$_3$), 149.0 (C=N), 153.8 (CO-Eoc), 156.0 (CO-Boc), 172.4 (COO$^t$Bu).

MS (ESI):
m/z=455 [M+Na]$^+$, 433 [M+H]$^+$, 377 [M-C$_4$H$_8$+H]$^+$.
$C_{19}H_{36}N_4O_7$ (432.52)

| | | | | | | |
|---|---|---|---|---|---|---|
| Calculated | C | 52.76 | H | 8.39 | N | 12.95 |
| Found | C | 53.65 | H | 8.57 | N | 13.24 |

$N^\omega$-ethoxycarbonyl-$N^{\omega'}$-methoxy-L-arginine Bis (trifluoracetate) (6)

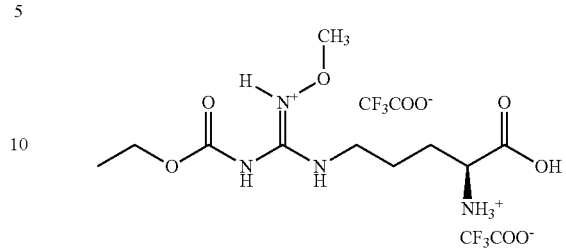

200 mg of the completely protected A'-methoxy-L-arginine 5 (0.46 mmol) are stirred in 5 mL of TFA at first for 30 minutes at 0° C. and then for three hours at room temperature. TFA is carefully distilled off at the lowest possible temperature in vacuum, and the residue is taken up with a little Aqua bidest. There follows a further purification by means of flash chromatography on an RP-18 column (0.1% of TFA in Aqua bidest.). The ninhydrine-positive fractions are combined, concentrated using the rotary evaporator at approximately 30° C. to a residual volume of approximately 10 mL and lyophilised.

Yield: 225 mg of a colourless oil (97%)

TLC: $R_f$=0.44 (i-propanol/water/acetic acid, 8:1:1, ninhydrine)

$^1$H-NMR (DMSO-d$_6$):

δ/ppm=1.22 (t, $^3$J=7.1 Hz, 3H, CH$_2$—CH$_3$), 1.50-1.87 (m, 4H, β,γ-CH$_2$), 3.12 (br t, 2H, N—CH$_2$), 3.62 (s, 3H, O—CH$_3$), 3.90 (m, 1H, α-CH), 4.13 (q, $^3$J=7.1 Hz, 2H, CH$_2$—CH$_3$), 7.35 (br s, 1H, NH), 8.28 (br s, 3H, NH$_3^+$).

$^{13}$C-NMR (DMSO-d$_6$):

δ/ppm=14.1 (CH$_2$—CH$_3$), 24.6 (γ-CH$_2$), 27.3 (β-CH$_2$), 40.6 (N—CH$_2$), 51.7 (α-CH), 61.6 (CH$_2$—CH$_3$), 62.1 (O—CH$_3$), 149.0 (C=N), 153.5 (CO-Eoc), 170.9 (CO).

HRMS (m/z):
calculated for $C_{10}H_{21}N_4O_5$ [M+H]$^+$=277.15065, found: 277.15049.
$C_{10}H_{20}N_4O_5 \cdot 2.0$ CF$_3$COOH $\cdot 0.4$ H$_2$O (513.56)

| | | | | | | |
|---|---|---|---|---|---|---|
| Calculated | C | 32.74 | H | 4.87 | N | 10.91 |
| Found | C | 32.44 | H | 4.69 | N | 10.53 |

$N^\omega$-ethoxycarbonyl-$N^{107'}$-methoxy-L-arginine-ethylester dihydrochloride (7)

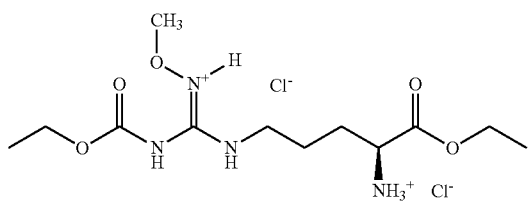 [SMILES: CCOC(=O)N/C(NCCC[C@H]([NH3+])C(=O)OCC)=[NH+]\OC ; [Cl-] ; [Cl-]]

For the esterification, 200 mg of the free amino acid 6 (0.397 mmol) are dissolved in 5 mL of absolute ethanol in an argon atmosphere. The solution is stirred at −10° C. for 30 minutes, before HCl gas is introduced into the solution for approximately 5-10 minutes. The batch is then stirred further for an hour at 0° C. and placed in the refrigerator for 36 hours. The solution is carefully concentrated in vacuum at room temperature and lyophilised. The product thus obtained is a very hygroscopic, amorph solid that liquefies on contact with air.

Yield: 150 mg of a colourless oil (99%)

$^1$H-NMR (DMSO-d$_6$):

δ/ppm=1.23, 1.25 (2×t, $^3$J=7.0 Hz, 3H, CH$_2$—CH), 1.55-1.88 (m, 4H, β,γ-CH$_2$), 3.32 (br t, 2H, N—CH$_2$), 3.71 (s, 3H, O—CH$_3$), 3.95 (m, 1H, α-CH), 4.19 (m, 4H, 2×CH$_2$—CH$_3$), 8.80 (br s, 4H, NH$_3^+$, NH).

$^{13}$C-NMR (DMSO-d$_6$):

δ/ppm=13.9, 14.0 (2×CH$_2$—CH$_3$), 24.0 (γ-CH$_2$), 26.9 (β-CH$_2$), 41.1 (N-CH$_2$), 51.4 (α-CH$_2$), 61.7, 62.5 (2×CH$_2$—CH$_3$), 63.9 (O—CH$_3$), 150.7 (C=N), 152.6 (CO-Eoc), 169.2 (COOEt).

HRMS (m/z):

calculated for C$_{12}$H$_{25}$N$_4$O$_5$ [M+H]$^+$=305.18195, found: 305.18176.

C$_{12}$H$_{24}$N$_4$O$_5$·2.0 HCl·0.6 H$_2$O (388.08)

| Calculated | C | 37.14 | H | 7.06 | N | 14.44 |
| Found | C | 36.67 | H | 7.59 | N | 15.00 |

Exemplary Embodiment 2: O-carboxyalkylated NOHA Derivatives

N$^ω$-benzyloxycarbonyl-N$^α$-(t-butyloxycarbonyl)-N$^{ω'}$-(methoxycarbonyl)methoxy-L-arginine-t-butylester (8)

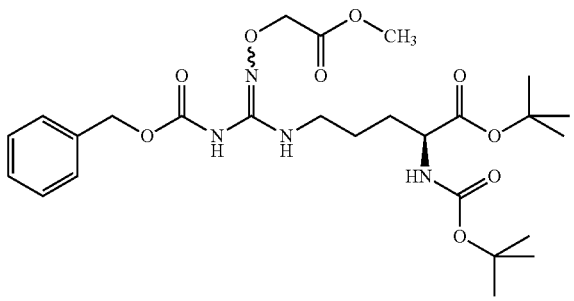 [SMILES: COC(=O)CON=C(NCCC[C@H](NC(=O)OC(C)(C)C)C(=O)OC(C)(C)C)NC(=O)OCc1ccccc1]

241 mg of the thiourea 1 (0.5 mmol) are dissolved in 5 mL of dry dichloromethane and 261 μL of DIPEA (0.75 mmol) and 79 mg of aminooxyacetic acid methylester (0.75 mmol) are added. The solution is brought to 0° C. for approximately 30 minutes and 143.5 mg of EDCl (0.75 mmol) are added. The mixture is stirred over night at room temperature. The solution is diluted with approximately 10 mL of dichloromethane and washed in each case with 5 mL of 1% HCl, water and saturated NaCl solution. The organic phase is dried over Na$_2$SO$_4$ and concentrated in vacuum. The raw product is purified further by means of chromatography over silica gel (cyclohexane/ethylacetate, 3:2).

Yield: 254 mg of a colourless oil (92%) TLC: R$_f$=0.48 (cyclohexane/ethylacetate, 3:2; ninhydrine)

$^1$H-NMR (CDCl$_3$):

δ/ppm=1.44, 1.46 (2×s, 9H, C(CH$_3$)$_3$), 1.50-1.87 (m, 4H, β,γ-CH$_2$), 3.07 (m, 2H, N—CH$_2$), 3.73 (s, 3H, O—CH$_3$), 4.16 (m, 1H, α-CH), 4.41 (s, 2H, O—CH$_2$), 5.08 (m, 1H, NH), 5.15 (s, 2H, CH$_2$-Cbz), 6.37 (br t, $^3$J=5.3 Hz, 1H, NH), 7.30-7.39 (m, 5H, ArH), 8.23 (br s, 1H, NH).

$^{13}$C-NMR (CDCl$_3$):

δ/ppm=25.5 (γ-CH$_2$), 28.7 (β-CH$_2$), 29.0, 30.9 (2× C(CH$_3$)$_3$), 41.2 (N—CH$_2$), 52.4 (O—CH$_3$), 54.5 (α-CH), 68.3 (CH$_2$-Cbz), 71.2 (O—CH$_2$), 80.3, 82.5 (2×C(CH$_3$)$_3$), 129.0, 129.28, 129.34 (ArCH), 135.9 (ArC), 150.8 (C=N), 153.7 (CO-Cbz), 156.0 (CO-Boc), 171.7, 172.4 (COO$^t$Bu, COOMe).

MS (ESI):

m/z=575 [M+Na]$^+$, 553 [M+H]$^+$, 497 [M–C$_4$H$_8$+H]$^+$.

N$^ω$-carboxymethoxy-L-arginine dihydrochloride (9)

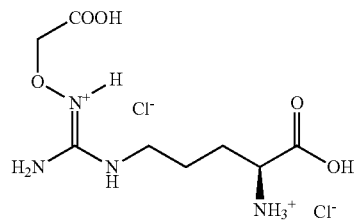

270 mg of the completely protected N$^ω$-carboxymethoxy-L-arginine 8 (0.489 mmol) are stirred at 50-60° C. for four hours in 5 mL of 6 N HCl. The batch is concentrated in vacuum, approximately 1-2 mL of *Aqua bidest.* are added, and it is then purified by means of flash chromatography on an RP-18 column (0.1% of TFA in *Aqua bidest.*). Ninhydrine-positive fractions are combined, concentrated using the rotary evaporator at 30° C. to only a few milliliters and then lyophilised.

Yield: 150 mg of a white, amorphous solid (96%)

TLC: R$_f$=0.53 (i-propanol/water/acetic acid, 6:3:1; ninhydrine) $^1$H-NMR (D$_2$O):

δ/ppm=1.76-2.18 (m, 4H, β,γ-CH$_2$), 3.41 (br t, $^3$J=6.7 Hz, 2H, N—CH$_2$), 4.17 (br t, $^3$J=6.2 Hz, α-CH), 4.63 (s, 2H, O—CH$_2$).

$^{13}$C-NMR (D$_2$O, TPS):

δ/ppm=26.3 (γ-CH$_2$), 29.6 (β-CH$_2$), 43.2 (N—CH$_2$), 55.3 (α-CH), 75.5 (O—CH$_2$), 161.0 (C=N), 174.6, 175.3 (2×CO).

MS (ESI):

m/z=249 [M+H]$^+$.

C$_8$H$_{16}$N$_4$O$_5$·2.0 HCl·0.5 H$_2$O (330.17)

| Calculated | C | 29.10 | H | 5.80 | N | 16.97 |
| Found | C | 29.00 | H | 5.99 | N | 17.16 |

N$^α$-(t-butyloxycarbonyl)-N$^ω$-ethoxycarbonyl-N$^{ω'}$-(ethoxycarbonyl)methoxy-L-arginine-t-butylester (10)

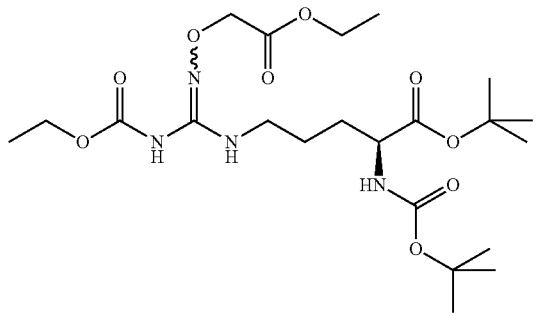 [SMILES: CCOC(=O)CON=C(NCCC[C@H](NC(=O)OC(C)(C)C)C(=O)OC(C)(C)C)NC(=O)OCC]

The preparation and working-up take place under the same conditions as described for the analogous compound 8, with the thiourea 2 and aminooxyacetic acid ethylester as starting substances (batch size: 1.0 mmol).

Yield: 500 mg of a colourless oil (99%)

TLC: $R_f$=0.51 (cyclohexane/ethylacetate, 3:2; ninhydrine)

$^1$H-NMR (CDCl$_3$):

δ/ppm=1.26 (t, $^3$J=7.1 Hz, 3H, CH$_2$—CH$_3$), 1.27 (t, $^3$J=7.1 Hz, 3H, CH$_2$-CH), 1.42, 1.44 (2×s, 9H, C(CH$_3$)$_3$), 1.51-1.85 (m, 4H, β,γ-CH$_2$), 3.06 (m, 2H, N—CH$_2$), 4.16 (q, $^3$J=7.11 Hz, 2H, CH$_2$—CH$_3$), 4.19 (q, $^3$J=7.17 Hz, 2H, CH$_2$—CH$_3$), 4.39 (s, 2H, O—CH$_2$), 5.08 (m, 1H, NH), 6.40 (br t, 1H, NH), 8.19 (br s, 1H, NH).

$^{13}$C-NMR (CDCl$_3$):

δ/ppm=14.1, 14.2 (2×CH$_2$—CH$_3$), 24.8 (γ-CH$_2$), 27.9, 28.3 (233 C(CH$_3$)$_3$), 30.2 (β-CH$_2$), 40.5 (N—CH$_2$), 53.7 (α-CH), 60.8, 61.9 (2×CH$_2$—CH$_3$), 70.7 (O—CH$_2$), 79.5, 81.8 (2×C(CH$_3$)$_3$), 150.4 (C=N), 153.2 (CO-Eoc), 155.3 (CO-Boc), 170.7, 171.7 (COOEt, COO$^t$Bu).

MS (ESI):

m/z=527 [M+Na]$^+$, 505 [M+H]$^+$, 449 [M–C$_4$H$_8$]$^+$.

C$_{22}$H$_{40}$N$_4$O$_9$ (504.59)

| Calculated | C | 52.37 | H | 7.99 | N | 11.10 |
| --- | --- | --- | --- | --- | --- | --- |
| Found | C | 53.09 | H | 7.90 | N | 11.44 |

N$^ω$-ethoxycarbonyl-N$^{ω'}$-(ethoxycarbonyl)methoxy-L-arginine bis(trifluoracetate) (11)

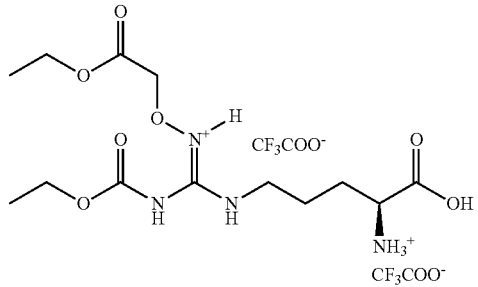

252 mg of the completely protected precursor 10 (0.5 mmol) are stirred in 5 mL of TFA at first at 0° C. for 30 minutes and then at room temperature for three hours. TFA is carefully distilled off at the lowest possible temperature in vacuum, and the residue is taken up with a little *Aqua bidest*. There follows the further purification by means of flash chromatography on an RP-18 column (0.1% TFA$_{(aq)}$/methanol step gradient, 5-30%). The ninhydrine-positive fractions are combined, concentrated using the rotary evaporator at approximately 30° C. to a residual volume of approximately 10 mL and lyophilised.

Yield: 277 mg of a clear oil (96%)

TLC: $R_f$=0.62 (i-propanol/water/acetic acid, 8:1:1; ninhydrine)

The substance is present as a solvent in DMSO-d$_6$ as an isomer mixture in a ratio of approximately 8.6:1.4 (at 300 K, relative to the singulet of CH$_2$ of the ethoxycarbonylmethoxy radical). The shifts specified refer to the main isomer.

$^1$H-NMR (DMSO-d$_6$):

δ/ppm=1.19 (t, $^3$J=7.10 Hz, 3H, CH$_2$—CH 1.21 (t, $^3$J=7.08 Hz, 3H, CH$_2$—CH$_3$), 1.48-1.87 (m, 4H, β,γ-CH$_2$), 3.02 (m, 2H, N—CH$_2$), 3.89 (m, 1H, α-CH), 4.10 (q, $^3$J=7.04 Hz, 2H, CH$_2$—CH$_3$), 4.12 (q, $^3$J=7.13 Hz, 2H, CH$_2$—CH$_3$), 4.37 (s, 2H, O—CH$_2$), 6.54 (br s, 1H, NH), 8.24 (br s, 3H, NH$_3^+$), 10.64 (br s, COOH).

$^{13}$C-NMR (DMSO-d$_6$):

δ/ppm=14.0, 14.2 (2×CH$_2$—CH$_3$), 27.4 (CH$_2$), 40.3 (N—CH$_2$), 51.8 (α-CH), 60.2, 61.3 (2×CH$_2$—CH$_3$), 70.3 (O—CH$_2$), 169.9, 171.0 (3×CO).

HRMS (m/z):

calculated for C$_{13}$H$_{25}$N$_4$O$_7$ [M+H]$^+$=349.17178, found: 349.17155.

C$_{13}$H$_{24}$N$_4$O$_7$·3.2 CF$_3$COOH·1.5 H$_2$O (740.26)

| Calculated | C | 31.48 | H | 4.11 | N | 7.57 |
| --- | --- | --- | --- | --- | --- | --- |
| Found | C | 31.52 | H | 4.24 | N | 7.40 |

N$^ω$-ethoxycarbonyl-N$^{ω'}$-(ethoxycarbonyl)methoxy-L-arginine-ethylester dihydrochloride (12)

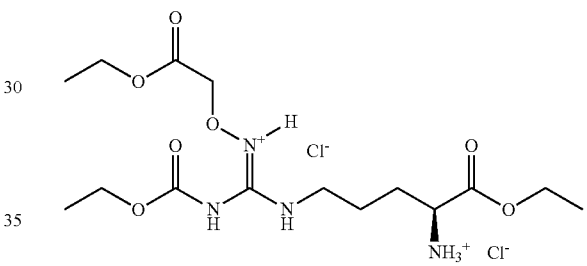

For the esterification, 288 mg of the free amino acid 11 (0.5 mmol) are dissolved in an argon atmosphere in 5 mL of absolute ethanol. The solution is stirred at 31 10° C. for 30 minutes, before HCl gas is introduced into the solution for approximately 5-10 minutes. The batch is then stirred further for an hour at 0° C. and placed in the refrigerator over night. The solution is carefully concentrated in vacuum at room temperature, lyophilised and yields a strongly hygroscopic, amorphous solid that liquefies on contact with air.

Yield: 222 mg of a colourless oil (99%)

TLC: $R_f$=0.57 (i-propanol/water/acetic acid, 8:1:1; ninhydrine)

$^1$H-NMR (DMSO-d$_6$):

δ/ppm=1.20 (t, $^3$J=7.16 Hz, 3H, CH$_2$—CH$_3$), 1.23 (t, $^3$J=7.13 Hz, 3H, CH$_2$—CH$_3$), 1.26 (t, $^3$J=7.10 Hz, 3H, CH$_2$—CH$_3$), 1.51-1.87 (m, 4H, β,γ-CH$_2$), 3.17 (m, 2H, N—CH$_2$), 3.95 (m, 1H, α-CH), 4.14 (q, $^3$J=7.12 Hz, 2H, CH$_2$—CH$_3$), 4.15 (q, $^3$J=7.10 Hz, 2H, CH$_2$—CH$_3$), 4.17-4.25 (m, 2H, CH$_2$—CH$_3$), 4.51 (s, 2H, O—CH$_2$), 7.80 (br s, 1H, NH), 8.55 (br s, 1H, NH), 8.72 (br s, 3H, NH$_3^+$).

$^{13}$C-NMR (DMSO-d$_6$):

δ/ppm=13.9, 14.0, 14.1 (3×CH$_2$—CH$_3$), 24.2 (γ-CH$_2$), 27.2 (β-CH$_2$), 40.8 (N—CH$_2$), 51.5 (α-CH), 60.5, 61.7, 61.9 (3×CH$_2$—CH$_3$), 71.1 (O—CH$_2$), 150.3 (C=N), 153.0 (CO—Eoc), 169.1, 169.3 (2×CO).

Exemplary Embodiment 3: O-Glycosidically Conjugated NOHA Derivatives

HRMS (m/z):

calculated for $C_{15}H_{29}N_4O_7$ [M+H]$^+$=377.20308, found: 377.20287.

$N^\alpha$-(t-butyloxycarbonyl)-$N^{\omega}$-ethoxycarbonyl-$N^{\omega'}$-(2,3,4,6-tetra-O-acetyl-β-D-galactopyranos-1-yl)oxy-L-arginine-t-butylester (13)

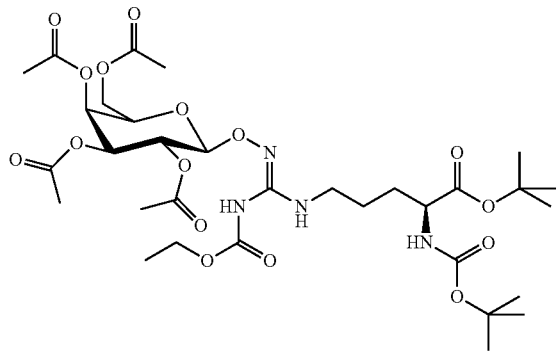

210 mg of the thiourea 2 (0.5 mmol), 218 mg of 1-aminooxy-2,3,4,6-tetra-O-acetyl-β-D-galactopyranose (0.6 mmol) and 104.5 µl of DIPEA (0.6 mmol) are dissolved in 5 mL of dry dichloromethane. The batch is cooled to 0° C., 115 mg of EDCl (0.6 mmol) are added and stirred at room temperature for 48 hours. The solution is diluted with approximately 10 mL of dichloromethane and in each case washed with 5 mL of 1% HCl, water and saturated NaCl solution. The organic phase is dried over $Na_2SO_4$ and concentrated in vacuum. The raw product is purified further by means of column chromatography over silica gel (dichloromethane/methanol, 97:3). The combined fractions of the purified product are concentrated in vacuum to form a clear oil. Repeatedly adding and removing dry dichloromethane yields a solid white foam that liquefies on contact with air.

Yield: 262 mg of a colourless oil (70%)

TLC: $R_f$=0.35 (dichloromethane/methanol, 97:3; ninhydrine)

$^1$H-NMR (CDCl$_3$):

δ/ppm=1.29 (t, $^3$J=7.1 Hz, 3H, CH$_2$—CH$_3$), 1.43, 1.45 (2×s, 9H, C(CH$_3$)$_3$), 1.52-1.86 (m, 4H, β,γ-CH$_2$), 1.98, 2.02, 2.05, 2.13 (4×COCH$_3$), 3.08 (m, 2H, N—CH$_2$), 3.96 (br t, $^3$J=6.8 Hz, 1H, 5'-CH), 4.11-4.21 (m, 5H, α-CH, CH$_2$—CH$_3$, 3'-CH, NH), 4.85 (d, $^3$J=8.3 Hz, 1H, 1'-CH), 5.06 (m, 2H, 6'-CH$_2$), 5.25 (dd, $^3$J=10.4, 8.3 Hz, 1H, 2'-CH), 5.39 (dd, $^3$J=3.5, 1.0 Hz, 1H, 4'-CH), 6.47 (br t, 1H, NH), 7.65 (br s, 1H, NH).

MS (ESI):

m/z=772 [M+Na]$^+$, 750 [M+H]$^+$, 707 [M−C$_2$H$_2$O+H]$^+$.

Sodium salt of the $N^{\omega}$-ethoxycarbonyl-$N^{\omega'}$-(2,3,4,6-tetra-O-acetyl-β-D-galactopyranos-1-yl)oxy-t-arginine (14)

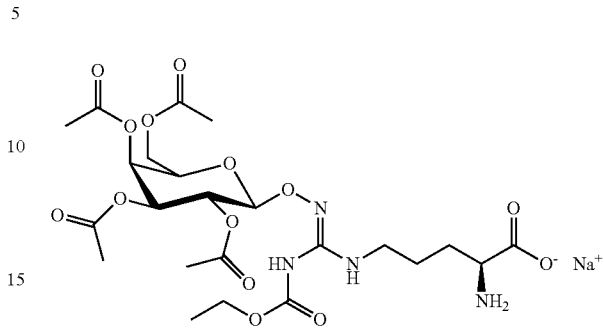

In a Schlenk tube 120 mg (0.16 mmol) of the completely protected and carefully dried precursor 13 are dissolved with argon fumigation in approximately 10 mL of dry diethylether. The solution is stirred for approximately 30 minutes at −15° C., and then HCl gas is introduced carefully with simultaneous argon fumigation for approximately 5 minutes. The reaction mixture is placed over night in the refrigerator and concentrated the following day for working up in vacuum. The white-yellow solid is then taken up with approximately 1-2 mL of 0.5 M NaHCO$_3$ solution and purified by means of flash chromatography over an RP-18 column (flow agent: *Aqua bidest.*/methanol), a step gradient being used for the elution. The start is made with a concentration of 10% methanol, then increased to 25% and finally to 50% methanol. The product-containing fractions are combined, concentrated at 30° C. in vacuum to a residual volume of approximately 50 mL and then lyophilised.

Yield: 74 mg of a fine white powder (75%)

In D$_2$O as solvent, the substance is present as an isomer mixture in a ratio of approximately 6:4 (at 300 K, relative to the triplet of CH$_3$ of the ethoxycarbonyl function). The shifts specified refer to the main isomer.

$^1$H-NMR (D$_2$O, TPS):

δ/ppm=1.28 (t, $^3$J=7.1 Hz, 3H, CH$_2$—CH$_3$), 1.52-1.97 (m, 4H, β,γ-CH$_2$), 2.02, 2.08, 2.12, 2.23 (4×s, 3H, COCH$_3$), 3.16 (br t, $^3$J=6.8 Hz, 2H, 6'-CH$_2$), 3.75 (t, $^3$J=6.3 Hz, 1H, 5'-CH), 4.15-4.30 (m, 5H, CH$_2$—CH$_3$, α-CH, N—CH$_2$), 5.07 (d, $^3$J=8.0 Hz, 1H, 1'-CH), 5.21-5.33 (m, 2H, 2',3'-CH), 5.47 (m, 1H, 4'-CH).

$^{13}$C-NMR (D$_2$O, TPS):

δ/ppm=16.2 (CH$_2$—CH$_3$), 22.7, 22.8, 22.9, (4×COCH$_3$), 26.6 (γ-CH$_2$), 30.6 (β-CH$_2$), 42.7 (N—CH$_2$), 57.2 (α-CH), 64.6 (6'-CH$_2$), 65.8 (CH$_2$—CH$_3$), 70.6, 70.7, 73.4, 74.1 (2', 3',4',5'-CH), 104.1 (1'-CH), 155.6 (C=N), 156.8 (CO-Eoc), 175.4, 175.8, 176.2, 177.1 (4×COCH$_3$).

MS (ESIESI):

m/z=615 [M+Na]$^+$, 593 [M+H]$^+$, 551 [M−C$_2$H$_2$O+H]$^+$, 331 [C$_{14}$H$_{19}$O$_9$]$^+$.

HRMS (m/z):

calculated for $C_{23}H_{33}N_4O_{14}Na$ [M+Na]$^+$=615.21202, found: 615.21164

$C_{23}H_{35}N_4NaO_{14}$ (614.53)

| | | | | | | |
|---|---|---|---|---|---|---|
| Calculated | C | 44.95 | H | 5.74 | N | 9.12 |
| Found | C | 45.08 | H | 6.21 | N | 8.77 |

The invention claimed is:

1. A method of treating a disease accompanying a nitrogen monoxide deficiency comprising: administering a pharmaceutical substance having the general formula (I)

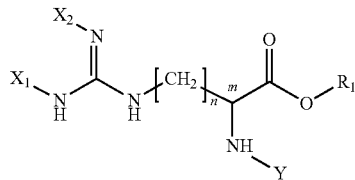

(I)

where
$X_1$ is H; $X_2$ is

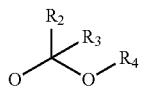

$R_1$ is ethyl;
$R_{2-4}$ is hydrogen, an alkyl, an aryl radical, a monosaccharide or a monosaccharide derivative;
Y is hydrogen;
n is 2 or 3;
m is an R or S configured chiral center;
and where $N^{\omega}$-hydroxy-L-arginine and its carboxylic acid ester are exempt, and wherein the disease accompanying a nitrogen monoxide deficiency is a cardiovascular disease.

2. The method according to claim 1, wherein $R_2$, $R_3$ and/or $R_4$ is a monosaccharide or a monosaccharide derivative.

3. The method according to claim 1 wherein the cardiovascular disease is selected from the group consisting of: high blood pressure, heart failure, stable and unstable angina pectoris, peripheral and cardial vessel diseases, arrhythmias, thromboembolic diseases and ischemias including myocardial infarcation, stroke, transient and ischemic attacks, peripheral circulatory disorders, restenoses after thrombolytic therapies, percutaneous transluminal angioplasties, percutaneous transluminal coronary angioplasties, or bypass, and atherosclerosis.

4. The method according to claim 1 wherein the pharmaceutical substance undergoes deprotection and functionalization.

5. The method of claim 1 wherein the pharmaceutical substance is a prodrug of NOHA.

* * * * *